United States Patent [19]

Lenker

[11] Patent Number: 5,044,422

[45] Date of Patent: Sep. 3, 1991

[54] CRYOGENIC PROCESSING OF ORTHOPEDIC IMPLANTS

[76] Inventor: Charles A. Lenker, 14264 12th Rd., Plymouth, Ind. 46563

[21] Appl. No.: 590,698

[22] Filed: Oct. 1, 1990

[51] Int. Cl.[5] .............................................. F25B 13/00
[52] U.S. Cl. .......................................... 165/2; 62/62; 62/78; 623/22
[58] Field of Search ........................ 623/22; 62/62, 78; 165/2

[56] References Cited

U.S. PATENT DOCUMENTS 4,878,916 11/1989 Rhenter et al. ........................ 623/22

Primary Examiner—Ronald C. Capossela
Attorney, Agent, or Firm—Michael I. Kroll

[57] ABSTRACT

A cryogenic method for strengthening an orthopedic implant prior to its use is disclosed. The cryogenic method for strengthening an orthopedic implant includes the steps of placing the orthopedic implant and/or the implant material in a treatment chamber which is kept at room temperature, applying the total number of temperature steps to the orthopedic implant, as a first variable, to bring the orthopedic impalant and/or the implant material in the treatment chamber to −320° F. or below, applying the total number of temperature steps to the orthopedic implant, as a second variable, to bring the orthopedic implant and/or the implant material in the treatment chamber to +295° F., or below, depending on material type, applying the total number of temperature steps to the orthopedic implant, as a third variable, to bring the orthopedic implant and/or the implant material in the treatment chamber to room temperature.

1 Claim, 2 Drawing Sheets

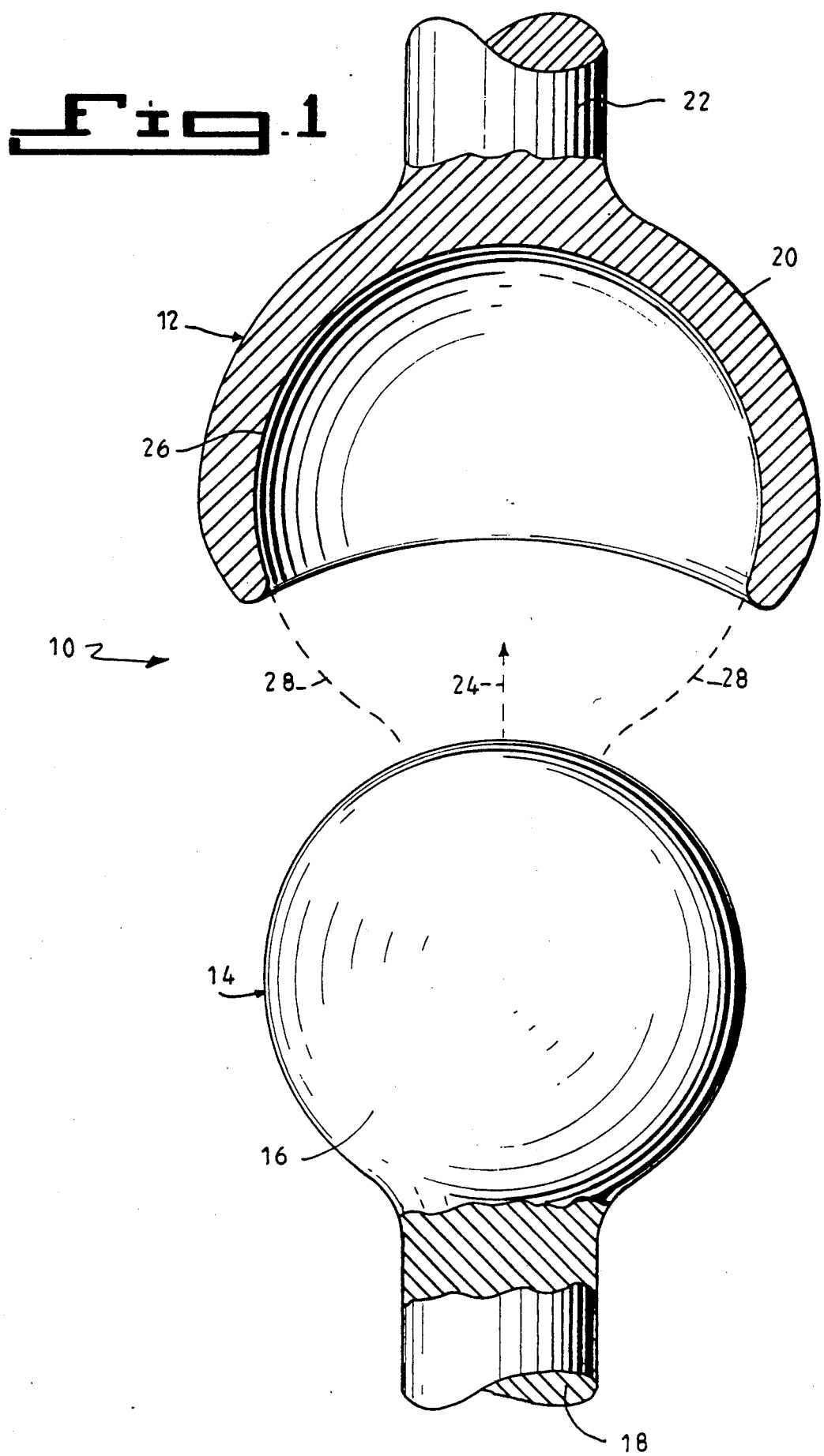

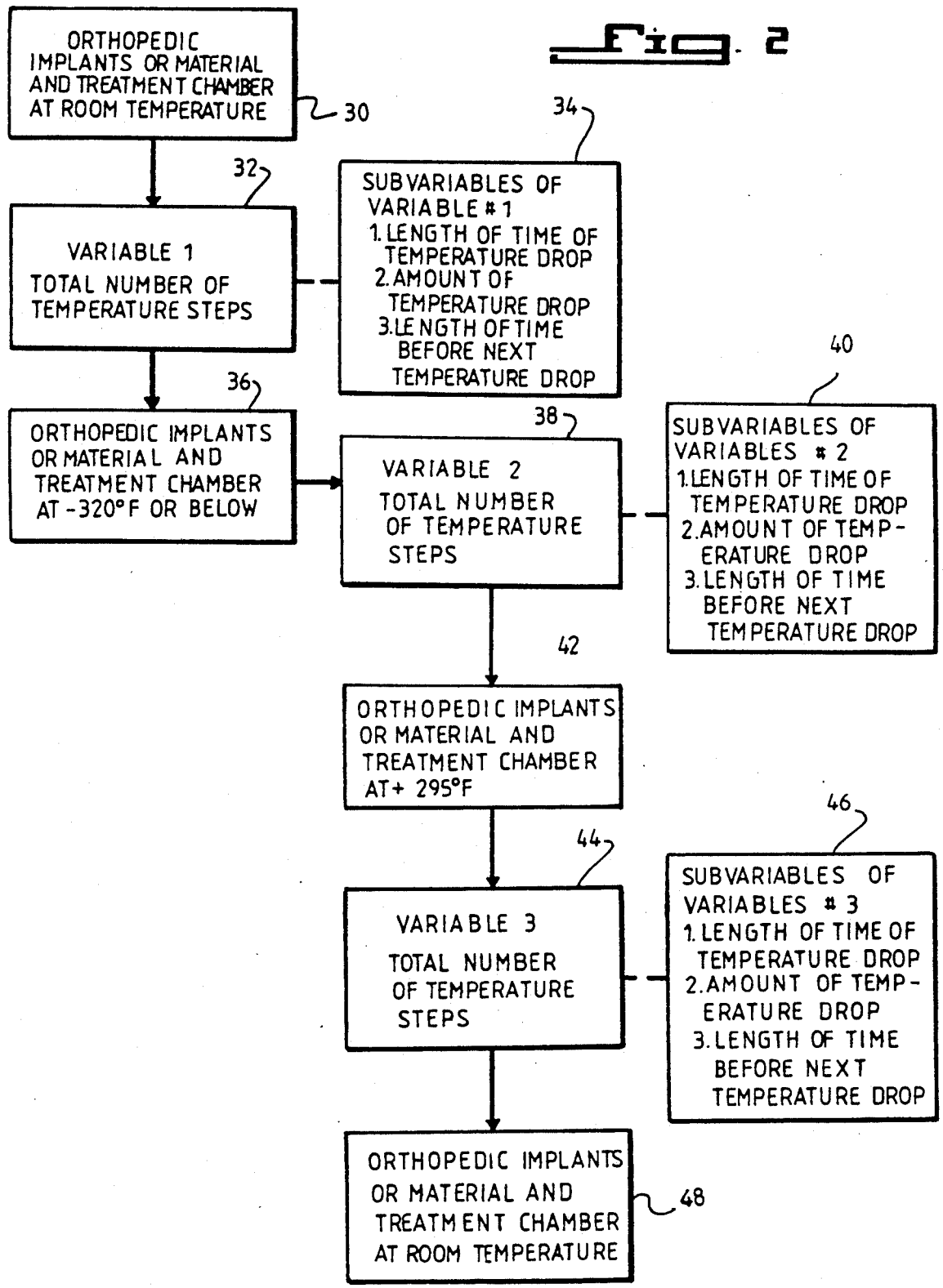

CRYOGENIC PROCESSING OF ORTHOPEDIC IMPLANTS

BACKGROUND OF THE INVENTION

1. Field of the Invention

The present invention relates to orthopedic implants. More particularly, the present invention relates to cryogenic processing of orthopedic implants.

2. Description of the Prior Art

Numerous innovations for orthopedic implants have been provided in the prior art that are adapted to be used. Even though these innovations may be suitable for the specific individual purposes to which they address, they would not be suitable for the purposes of the present invention as heretofore described.

SUMMARY OF THE INVENTION

Accordingly, it is an object of the present invention to provide a cryogenic processes for orthopedic implants that avoids the disadvantages of the prior art.

More particularly, it is an object of the present invention to provide the cryogenic processing of orthopedic products that are to be used internal to the body. This novel process of the present invention would be applied to all types of metals and/or composite materials for use in, but not limited to, the most common implants, that is full hip replacements and full knee replacements, as well as synthetic materials.

The cryogenic processing of the present invention involves placing the parts of the implants to be treated in a treatment chamber. The parts in the treatment chamber are subjected to a specific temperature and time profile. The profile ranges from room temperature at initiation, to $-310°$ F. or below (depending on the material), then to $295°$ F. or below (depending on the material), and then back to room temperature. This process would take a period lasting from several hours to two and one half days, depending on material type and the quantity being treated, to be completed.

In keeping with these objects, and with others which will become apparent hereinafter, one feature of the present invention resides, briefly stated, in a cryogenic method for strengthening and/or changing the modulus of elasticity of an orthopedic implant prior to use, including the steps of, placing the orthopedic implant and/or implant material in a treatment chamber which is at room temperature, applying the total number of temperature steps to the orthopedic implant — as a first variable, to bring the orthopedic implant and/or implant material in the treatment chamber to $-320°$ F. or below, applying the total number of temperature steps to the orthopedic implant — as a second variable, to bring the orthopedic implant and/or implant material in the treatment chamber to $+295°$ F., applying the total number of temperature steps to the orthopedic implant — as a third variable, to bring the orthopedic implant and/or implant material in the treatment chamber to.

When the cryogenic processing of orthopedic implants is designed in accordance with the present invention, the orthopedic implant pieces become strangers.

In accordance with another feature of the present invention, the steps of applying the total number of temperature steps to the orthopedic implants vary the length of time of the temperature drops, the amount of the temperature drop, and the length of time before the next temperature drop.

The novel features which are considered characteristic for the invention are set forth in particular in the appended claims. The invention itself, however, both as to its construction and its method of operation, together with additional objects and advantages thereof, will be best understood from the following description of the specific embodiments when read in connection with the accompanying drawing.

BRIEF DESCRIPTION OF THE DRAWING

FIG. 1 is a partial cross-sectional view of a typical ball and socket of an orthopedic implant that can use the present invention; and FIG. 2 is a flow chart indicating the steps necessary for carrying out the method of the present invention.

LIST OF REFERENCE NUMERALS UTILIZED IN THE DRAWING

10 — typical ball socket of an orthopedic implant

12 — socket portion of the cryogenic processing of orthopedic implants 10 of the present invention 14 — ball portion of the cryogenic processing of orthopedic implants 10 of the present invention 16 — spherical part of the ball portion 14

18 — solid shaft part of the ball portion 14

20 — hollow substantially spherical part of the socket portion 12

22 — solid shaft part of the socket portion 12

24 — phantom arrow indicating the position of assembly of the cryogenic processing of orthopedic implants 10

26 — socket portion 12 in solid lines

28 — ball portion 14 in phantom lines

30 — first box of the flow chart of FIG. 2

32 — second box of the flow chart of FIG. 2

34 — third box of the flow chart of FIG. 2

36 — fourth box of the flow chart of FIG. 2

38 — fifth box of the flow chart of FIG. 2

40 — sixth box of the flow chart of FIG. 2

42 — seventh box of the flow chart of FIG. 2

44 — eighth box of the flow chart of FIG. 2

46 — ninth box of the flow chart of FIG. 2

48 — tenth box of the flow chart of FIG. 2

DETAILED DESCRIPTION OF THE PREFERRED EMBODIMENT

Cryogenic processing of orthopedic implants enhances the properties of the treated material by relief of residual stresses incurred in manufacturing or material origination, as well as changes in the micro structure of the implant or implant material, including but not limited to grain growth in the metals, composites or synthetic materials such as polymers and plastics. The changes produce increased mudulus (flexibility) and greater resistance to wear. Some materials also machine with less resistance. There is enhanced dimensional stability during the manufacturing process of parts made from cyrogenically treated materials.

Referring now to FIG. 1, where a typical ball socket of a cryogenic processing of an orthopedic implant 10, is shown in partial cross-section. The typical ball socket of an orthopedic implant 10 includes a socket portion 12 and a ball portion 14.

As shown, the ball portion 14 includes a spherical part 16 onto which is disposed a solid shaft part 18. The spherical part 16 and the shaft part 18 are formed as one homogeneous part so that the spherical part 16 and the shaft part 18 contain no joints that could weaken the ball portion 14 and cause possible failure.

The socket portion 12 includes a hollow substantially spherical part 20 onto which is disposed a solid shaft part 22. The hollow spherical part 20 and the solid shaft part 22 are also formed as one homogeneous part so that the hollow spherical part 20 and the shaft part 22 contain no joints that could weaken the socket portion 12 and cause possible failure.

Even in view of the above, some constructions include multiple parts without degradation.

The hollow spherical part 20 contains some degree of resiliency. The resiliency of the hollow spherical part 20 allows the ball portion 14 to snap into the socket portion 12, from the direction of the phantom arrow 24, in order to form the typical ball socket 10 shown with the socket portion 12 in solid lines 26 and the ball portion 14 in phantom lines 28. The result is that the typical ball socket 10 implant has 360° of rotational movement in all shear planes and, if necessary, minimal rectilinear movement.

To better define the method of the present invention, a detailed flow chart is included as FIG. 2. Each box of the flow chart will be discussed, one by one for simplicity.

There is only one treatment chamber. The parts and chamber begin the process at room temperature. The process then continues to get the internal chamber temperature (and parts or material) to −320° F. or below, (depending on material). Then to +295° F. or lower, depending on material. Then back down to room temperature all without removing the parts from the chamber.

The first box 30, of the flow chart of FIG. 2, represents the treatment chamber, at room temperature, with the orthopedic material and/or the orthopedic implants.

The second box 32, of the flow chart of FIG. 2, represents the first variable, that is the total number of temperature steps necessary to reach the desired cryogenic temperature in the treatment chamber.

The third box 34, of the flow chart of FIG. 2, represents the subvariables of the first variable, including the length of time of the temperature drop, the amount of the temperature drop, and the length of time before the next temperature drop.

The fourth box 36, of the flow chart of FIG. 2, represents the treatment chamber, now at −320° F. or below, with the orthopedic material and/or the orthopedic implants.

The fifth box 38, of the flow chart of FIG. 2, represents the second variable, that is the total number of temperature steps necessary to reach the desired cryogenic temperature.

The sixth box 40, of the flow chart of FIG. 2, represents the subvariables of the second variable, including the length of time of the temperature drop, the amount of the temperature drop, and the length of time before the next temperature drop.

The seventh box 42, of the flow chart of FIG. 2, represents the treatment chamber, now at +295° F. with the orthopedic material and/or the orthopedic implants.

The eighth box 44, of the flow chart of FIG. 2, represents the third variable, that is the total number of temperature steps necessary to reach the desired cryogenic temperature.

The ninth box 46, of the flow chart of FIG. 2, represents the subvariables of the third variable including, the length of time of the temperature drop, amount of the temperature drop, and the length of time before the next temperature drop.

The tenth and final box 48, of the flow chart of FIG. 2, represents the treatment chamber, now at room temperature with the orthopedic material and/or the orthopedic implants.

It will be understood that each of the elements described above, or two or more together, may also find a useful application in other types of constructions differing from the type described above.

While the invention has been illustrated and described as embodied in an orthopedic implant, it is not intended to be limited to the details shown, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

1. A cryogenic method for strengthening and improving wearibility and longevity of orthopedic implant and implant material prior to its use, comprising the steps of:
 a) placing the orthopedic implant and implant material in a treatment chamber which is kept at room temperature;
 b) cooling the implant and implant material to a temperature of at least −320° F.;
 c) heating the cooled implant and implant material to a temperature of at least +295° F.;
 d) bringing the implant and implant material back to room temperature.

* * * * *